US008026082B2

(12) United States Patent
Bryan et al.

(10) Patent No.: US 8,026,082 B2
(45) Date of Patent: Sep. 27, 2011

(54) SYNTHETIC GENE CONTROL REGION

(75) Inventors: Janine Bryan, Furlong, PA (US);
Michelle K. Brownlow, Jamison, PA (US); Loren D. Schultz, Harleysville, PA (US); Maria C. Losada, Union, NJ (US); Kathrin Ute Jansen, Allendale, NJ (US); Myra Kurtz, Martinsville, NJ (US); Stuart Kurtz, legal representative, Martinsville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 431 days.

(21) Appl. No.: 11/921,903

(22) PCT Filed: Jun. 9, 2006

(86) PCT No.: PCT/US2006/022489
§ 371 (c)(1),
(2), (4) Date: Dec. 10, 2007

(87) PCT Pub. No.: WO2006/138167
PCT Pub. Date: Dec. 28, 2006

(65) Prior Publication Data
US 2010/0041097 A1 Feb. 18, 2010

Related U.S. Application Data

(60) Provisional application No. 60/690,321, filed on Jun. 14, 2005.

(51) Int. Cl.
*C12P 21/02* (2006.01)
(52) U.S. Cl. .............. 435/69.1; 435/320.1; 435/254.21; 536/24.1
(58) Field of Classification Search .................. None
See application file for complete search history.

(56) References Cited

U.S. PATENT DOCUMENTS

| 5,068,185 A | 11/1991 | Hopper et al. | |
|---|---|---|---|
| 5,407,822 A | 4/1995 | Leplatois et al. | |
| 5,543,322 A * | 8/1996 | Kitano et al. | 435/252.3 |
| 5,820,870 A | 10/1998 | Joyce et al. | |

FOREIGN PATENT DOCUMENTS

| EP | 0 258 067 B1 | 3/1993 |
|---|---|---|
| WO | WO 96/26413 A2 | 9/1996 |
| WO | WO 2005/095608 A1 | 10/2005 |

OTHER PUBLICATIONS

Lo Presti et al., Research in Microbiology, vol. 160 (2009) pp. 380-388.*
Bram et al., "A *GAL* family of upstream activating sequences in yeast: roles in both induction and repression of transcription", The EMBO Journal, vol. 5, pp. 603-608 (1986).
Buckholz et al., "Yeast Systems for the Commercial Production of Heterologous Proteins", Bio/Technology, vol. 9, pp. 1067-1072 (1991).
Carraro et al., "A Region of the Cellobiohydrolase I Promoter from the Filamentous Fungus *Trichoderma reesei* Mediates Glucose Repression in *Saccharomyces cerevisiae*, Dependent on Mitochondrial Activity", Biochemical and Biophysical Research Communications, vol. 253, pp. 407-414 (1998).
Chavez et al., "Structure analysis of the endoxylanase A gene from *Penicillium purpurogenum*", Biol. Res., vol. 34, pp. 217-226 (2001).
Cregg et al., "Recombinant Protein Expression in *Pichia pastoris*", Molecular Biotechnology, vol. 16, pp. 23-52 (2000).
Dominguez et al., "Non-conventional yeasts as hosts for heterologous protein production", International Microbiology, vol. 1, pp. 131-142 (1998).
Gellissen et al., "Application of yeasts in gene expression studies: a comparison of *Saccharomyces cerevisiae*, *Hansenula polymorpha* and *Kluyveromyces lactis*—a review", Gene, vol. 190, pp. 87-97 (1997).
Hofmann et al., "Sequence Determination of Human Papillomavirus Type 6a and Assembly of Virus-like Particles in *Saccharomyces cerevisiae*", Virology, vol. 209, pp. 506-518 (1995).
Johnston et al. "Sequences That Regulate the Divergent *GAL1-GAL10* Promoter in *Saccharomyces cerevisiae*", Molecular and Cellular Biology, vol. 4, pp. 1440-1448 (1984).
Lohr et al., Transcriptional regulation in the yeast *GAL* gene family: a complex genetic network, FASEB J., vol. 9, pp. 777-787 (1995).
Madzak et al., Heterologous protein expression and secretion in the non-conventional yeast *Yarrowia lipolytica*: a review, Journal of Biotechnology, vol. 109, pp. 63-81 (2004).
Melcher et al., "Zero Background Yeast Reporter Plasmids", Gene, vol. 247, pp. 53-61 (2000).
Muller, et al., Comparison of Expression Systems in the Yeasts *Saccharomyces cerevisiae*, *Hansenula polymorpha*, *Klyveromyces lactis*, *Schizosaccharomyces pombe* and *Yarrowia lipolytica*. Cloning of Two Novel Promoters from *Yarrowia lipolytica*, Yeast, vol. 14, pp. 1267-1283 (1998).
Nehlin et al., "Control of yeast *GAL* genes by MIG1 repressor: a transcriptional cascade in the glucose response", The EMBO Journal, vol. 10, pp. 3373-3377 (1991).
Romanos et al., "Foreign Gene Expression in Yeast: a Review", Yeast, vol. 8, pp. 423-488 (1992).
Upshall et al., "Molecular analysis of the *argB* gene of *Aspergillus nidulans*", Mol. Gen. Genet., vol. 204, pp. 349-354 (1986).
Werten et al., "High-yield Secretion of Recombinant Gelatins by *Pichia pastoris*", Yeast, vol. 15, pp. 1087-1096 (1999).
West et al., "*Saccharomyces cerevisiae GAL1-GAL10* Divergent Promoter Region: Location and Function of the Upstream Activating Sequence UASg", Molecular and Cellular Biology, vol. 4, pp. 2467-2478 (1984).
Zimmerman, et al., "The Isolation of a Dol-P-Man Synthase from *Ustilago maydis* that Functions in *Saccharomyces cerevisiae*", Yeast, vol. 12, pp. 765-771 (1996).

* cited by examiner

*Primary Examiner* — Jim Ketter
(74) *Attorney, Agent, or Firm* — Alysia A. Finnegan; Sheldon O. Heber

(57) ABSTRACT

The present invention provides a synthetic gene control region which comprises a gene regulatory sequence comprising a binding site for a gene regulatory protein of a yeast strain, and a promoter from filamentous fungal strain located downstream of the gene regulatory sequence; wherein the promoter can be recognized by the general transcription factors and RNA polymerase of the yeast strain; wherein the gene regulatory sequence is capable of regulating transcription initiated by the filamentous fungal promoter in the yeast strain.

18 Claims, 10 Drawing Sheets

```
  1 GGATATTCGT TTAGTTAGCC CCTCTACTAT GACATTACTT CTCCTGGGAT
    CCTATAAGCA AATCAATCGG GGAGATGATA CTGTAATGAA GAGGACCCTA
 51 GGTGACTACG ATCTTGTATA AGTATCAGGG TTGATCCCTC CAAATGATAG
    CCACTGATGC TAGAACATAT TCATAGTCCC AACTAGGGAG GTTTACTATC
101 CTTTCTTCAA CATCGACTCT CATAATCGAT ATACTTGAAA ACCCAACACA
    GAAAGAAGTT GTAGCTGAGA GTATTAGCTA TATGAACTTT TGGGTTGTGT
151 TCACTCAAA
    AGTGAGTTT
```

Figure 1A

```
  1  TTGACGACAC  AACCACGGAG  CGGGTGTTAC  TTCTTCTCAC  TCACGATTCT
     AACTGCTGTG  TTGGTGCCTC  GCCCACAATG  AAGAAGAGTG  AGTGCTAAGA
 51  CGATTCTCGA  TTCACGGTTC  TCGATTCTCG  CCGTCTTGGT  CTTTGGGAAG
     GCTAAGAGCT  AAGTGCCAAG  AGCTAAGAGC  GGCAGAACCA  GAAACCCTTC
101  GATCAGCTGC  CGAGCTGGAC  CACCGACCAC  CATCGGTCTT  AGCTACAACA
     CTAGTCGACG  GCTCGACCTG  GTGGCTGGTG  GTAGCCAGAA  TCGATGTTGT
151  ACCGCTCCAA  ATCACTCATA  CACGTCTAGA  ATCTCA
     TGGCGAGGTT  TAGTGAGTAT  GTGCAGATCT  TAGAGT
```

Figure 1B

```
  1 AAGCTTTATT TCGCGGTTTT TTGGGGTAGT CATCTAATGA AACAGACCCG
    TTCGAAATAA AGCGCCAAAA AACCCCATCA GTAGATTACT TTGTCTGGGC
 51 GACGCAGCAG AGGAAGCCCC GCGATGACTC TATACCACCG TACGCCGATA
    CTGCGTCGTC TCCTTCGGGG CGCTACTGAG ATATGGTGGC ATGCGGCTAT
101 TATCATCATC GCGGCGATGG AGAAGTGGGG TTGACTCCGA AGACACTTCA
    ATAGTAGTAG CGCCGCTACC TCTTCACCCC AACTGAGGCT TCTGTGAAGT
151 AAGGAGCGAC GCTGTTGATT TGTAGACGAC GCTTGATAGG GAGAAGCATT
    TTCCTCGCTG CGACAACTAA ACATCTGCTG CGAACTATCC CTCTTCGTAA
201 ATTGTCGTGA TGCTCGCCCA ACAGAGGCCG ACTCGCCTCA TCCGTCATAA
    TAACAGCACT ACGAGCGGGT TGTCTCCGGC TGAGCGGAGT AGGCAGTATT
251 CGAACGCTGT GTAAAGCGGA GTGGGGGGGA AAGTGTGGAT TGTGGAGAGT
    GCTTGCGACA CATTTCGCCT CACCCCCCCT TTCACACCTA ACACCTCTCA
301 ATGCGATAGT GTTGAGGCTG ATCAGACGGC GAATCGGGCC AGATATGACC
    TACGCTATCA CAACTCCGAC TAGTCTGCCG CTTAGCCCGG TCTATACTGG
351 AGTTTAGAGG CCTCATTTGA CTATAATTTA CATAAATTAG ATAAATAGAG
    TCAAATCTCC GGAGTAAACT GATATTAAAT GTATTTAATC TATTTATCTC
401 ATGAACGCAT GCAATAATTG CAGCAAATAT TGATGAAGCG AGAGGTAGGA
    TACTTGCGTA CGTTATTAAC GTCGTTTATA ACTACTTCGC TCTCCATCCT
451 CGATGAAGGA CTGTGAGCAG TTCAAGGTAT CAGCAGAGTC AAGGGCCTGA
    GCTACTTCCT GACACTCGTC AAGTTCCATA GTCGTCTCAG TTCCCGGACT
501 TGCAATGGCG GTGATCCGTG ATCAGCGAAC GGAAGGGGCG CTAACTCTGT
    ACGTTACCGC CACTAGGCAC TAGTCGCTTG CCTTCCCCGC GATTGAGACA
551 TTCTTTACCA ATGATCGGAA GCTCCTGCTG GCGGACTTAT GAGTCATTCA
    AAGAAATGGT TACTAGCCTT CGAGGACGAC CGCCTGAATA CTCAGTAAGT
601 CGAATCATTT CTCAGTTATT TGTGGATGCC CTCGTTCTGT CCACAATTTC
    GCTTAGTAAA GAGTCAATAA ACACCTACGG GAGCAAGACA GGTGTTAAAG
651 TTTCCGCCCC AAGTCTTTTA AGTTCTTTAA CATCTATATT CTTGCACTTC
    AAAGGCGGGG TTCAGAAAAT TCAAGAAATT GTAGATATAA GAACGTGAAG
701 CA
    GT
```

Figure 1C

```
                     GAL4                                                  GAL4
  1  GACAGCCCTC  GGAGCACTCT  CCTCCGTCCG  TGACCGTCAG  GTCGAGGCCA
     CTGTCGGGAG  CCTCGTGAGA  GGAGGCAGGC  ACTGGCAGTC  CAGCTCCGGT
                                                           GAL4
 51  TCCCGATGCA  CTTACATCAG  GTCCGCTCGT  GCCTTACTAA  TCCGGAGGAC
     AGGGCTACGT  GAATGTAGTC  CAGGCGAGCA  CGGAATGATT  AGGCCTCCTG
101  TGTCCTCCGA  TCTATTGACG  TATTTACGTA  TACTAGGAGA  ATAAATCCGT
     ACAGGAGGCT  AGATAACTGC  ATAAATGCAT  ATGATCCTCT  TATTTAGGCA
                         MIG1
151  GATAGCTCGC  CCCGGTATGC  AATCATTCTA  CATACGTTAA  AATCGAACTA
     CTATCGAGCG  GGGCCATACG  TTAGTAAGAT  GTATGCAATT  TTAGCTTGAT
201  CGAATATAGG  ATCGTTTTTC  AATTTACGGA  TATTCTGGTG  GTATTATTAT
     GCTTATATCC  TAGCAAAAAG  TTAAATGCCT  ATAAGACCAC  CATAATAATA
        MIG1                                               MIG1
251  TATGTGGGGT  GTTAATTTCT  AGGGATATTC  GTTTAGTTAG  CCCCTCTACT
     ATACACCCCA  CAATTAAAGA  TCCCTATAAG  CAAATCAATC  GGGGAGATGA
301  ATGACATTAC  TTCTCCTGGG  ATGGTGACTA  CGATCTTGTA  TAAGTATCAG
     TACTGTAATG  AAGAGGACCC  TACCACTGAT  GCTAGAACAT  ATTCATAGTC
351  GGTTGATCCC  TCCAAATGAT  AGCTTTCTTC  AACATCGACT  CTCATAATCG
     CCAACTAGGG  AGGTTTACTA  TCGAAAGAAG  TTGTAGCTGA  GAGTATTAGC
401  ATATACTTGA  AAACCCAACA  CATCACTCAA  A
     TATATGAACT  TTTGGGTTGT  GTAGTGAGTT  T
```

Figure 2A

```
              GAL4
  1 GACAGCCCTC GGAGCACTCT CCTCCGAGCG TGAGCCTCAG GTCGAGGCCA
    CTGTCGGGAG CCTCGTGAGA GGAGGCTCGC ACTCGGAGTC CAGCTCCGGT
                                                    GAL4
 51 TCGCGATGCA CTTACATCAG GTGCGCTCGT GCGTTACTAA TGCGGAGGAC
    AGCGCTACGT GAATGTAGTC CACGCGAGCA CGCAATGATT ACGCCTCCTG
101 TGTCCTCCGA TCTATTGACG TATTTACGTA TACTAGGAGA ATAAATCGCT
    ACAGGAGGCT AGATAACTGC ATAAATGCAT ATGATCCTCT TATTTAGCGA
                        MIG1
151 GATAGCTCGC CCCGGTATGC AATCATTCTA CATACGTTAA AATCGAACTA
    CTATCGAGCG GGGCCATACG TTAGTAAGAT GTATGCAATT TTAGCTTGAT
201 CGAATATAGG ATCGTTTTTC AATTTACGGA TATTCTGGTG GTATTATTAT
    GCTTATATCC TAGCAAAAAG TTAAATGCCT ATAAGACCAC CATAATAATA
       MIG1                                         MIG1
251 TATGTGGGGT GTTAATTTCT AGGGATATTC GTTAGTTAG CCCCTCTACT
    ATACACCCCA CAATTAAAGA TCCCTATAAG CAAATCAATC GGGGAGATGA
301 ATGACATTAC TTCTCCTGGG ATGGTGACTA CGATCTTGTA TAAGTATCAG
    TACTGTAATG AAGAGGACCC TACCACTGAT GCTAGAACAT ATTCATAGTC
351 GGTTGATCCC TCCAAATGAT AGCTTTCTTC AACATCGACT CTCATAATCG
    CCAACTAGGG AGGTTTACTA TCGAAAGAAG TTGTAGCTGA GAGTATTAGC
401 ATATACTTGA AAACCCAACA CATCACTCAA A
    TATATGAACT TTTGGGTTGT GTAGTGAGTT T
```

Figure 2B

```
                    GAL4                                              GAL4
  1  GACAGCCCTC GGAGCACTCT CCTCCGTCCG TGACCGTCAG GTCGAGGCCA
     CTGTCGGGAG CCTCGTGAGA GGAGGCAGGC ACTGGCAGTC CAGCTCCGGT
                                                         GAL4
 51  TCCCGATGCA CTTACATCAG GTCCGCTCGT GCCTTACTAA TCCGGAGGAC
     AGGGCTACGT GAATGTAGTC CAGGCGAGCA CGGAATGATT AGGCCTCCTG
101  TGTCCTCCGA TCTATTGACG TATTTACGTA TACTAGGAGA ATAAATCGCT
     ACAGGAGGCT AGATAACTGC ATAAATGCAT ATGATCCTCT TATTTAGCGA
                                         MIG1
151  GATAGCTCAT CATTCTATGC AATCATTCCC CAGATTTTGC TATCGAACTA
     CTATCGAGTA GTAAGATACG TTAGTAAGGG GTCTAAAACG ATAGCTTGAT
201  CGAATATAGG ATCGTTTAAC AATTTACGGT TTTTCTGGTG GTATTAGCAA
     GCTTATATCC TAGCAAATTG TTAAATGCCA AAAAGACCAC CATAATCGTT
     MIG1
251  AATCTGGGGA ATTAATTGTC CACGAGCAGG ATTTTTTGTC AGGATATTCG
     TTAGACCCCT TAATTAACAG GTGCTCGTCC TAAAAAACAG TCCTATAAGC
                   MIG1
301  TTTAGTTAGC CCCTCTACTA TGACATTACT TCTCCTGGGA TGGTGACTAC
     AAATCAATCG GGGAGATGAT ACTGTAATGA AGAGGACCCT ACCACTGATG
351  GATCTTGTAT AAGTATCAGG GTTGATCCCT CCAAATGATA GCTTTCTTCA
     CTAGAACATA TTCATAGTCC CAACTAGGGA GGTTTACTAT CGAAAGAAGT
401  ACATCGACTC TCATAATCGA TATACTTGAA AACCCAACAC ATCACTCAAA
     TGTAGCTGAG AGTATTAGCT ATATGAACTT TTGGGTTGTG TAGTGAGTTT
```

Figure 2C

```
                   GAL4
  1  GACAGCCCTC GGATGACACT CCTCCGAGCG TGAGCCTCAG GTAGAGGCCA
     CTGTCGGGAG CCTACTGTGA GGAGGCTCGC ACTCGGAGTC CATCTCCGGT
                                                      GAL4
 51  TCGCGATGCA CTTACATCAG GTGCGCTCGT GCGTTACTAA TGCGGGCCAC
     AGCGCTACGT GAATGTAGTC CACGCGAGCA CGCAATGATT ACGCCCGGTG
101  TGTCGTCCGA TCTATTGACG TATTTACGTA TACTAGGAGA ATAAATCCGT
     ACAGCAGGCT AGATAACTGC ATAAATGCAT ATGATCCTCT TATTTAGGCA
                      MIG1
151  GATAGCTCGC CCCGGTATGC AATCATTCTA CATACGTTAA AATCGAACTA
     CTATCGAGCG GGGCCATACG TTAGTAAGAT GTATGCAATT TTAGCTTGAT
201  CGAATATAGG ATCGTTTTTC AATTTACGGA TATTCTGGTG GTATTATTAT
     GCTTATATCC TAGCAAAAAG TTAAATGCCT ATAAGACCAC CATAATAATA
        MIG1                                         MIG1
251  TATGTGGGGT GTTAATTTCT AGGGATATTC GTTTAGTTAG CCCCTCTACT
     ATACACCCCA CAATTAAAGA TCCCTATAAG CAAATCAATC GGGGAGATGA
301  ATGACATTAC TTCTCCTGGG ATGGTGACTA CGATCTTGTA TAAGTATCAG
     TACTGTAATG AAGAGGACCC TACCACTGAT GCTAGAACAT ATTCATAGTC
351  GGTTGATCCC TCCAAATGAT AGCTTCTTC AACATCGACT CTCATAATCG
     CCAACTAGGG AGGTTTACTA TCGAAGAAG TTGTAGCTGA GAGTATTAGC
401  ATATACTTGA AAACCCAACA CATCACTCAA A
     TATATGAACT TTTGGGTTGT GTAGTGAGTT T
```

Figure 2D

```
            GAL4
  1 GACAGCCCTC GGATGACACT CCTCCGAGCG TGAGCCTCAG GTCGAGGCCA
    CTGTCGGGAG CCTACTGTGA GGAGGCTCGC ACTCGGAGTC CAGCTCCGGT
                                                    GAL4
 51 TCGCGATGCA CTTACATCAG GTGCGCTCGT GCGTTACTAA TGCGGGCCAC
    AGCGCTACGT GAATGTAGTC CACGCGAGCA CGCAATGATT ACGCCCGGTG
101 TGTCGTCCGA TCTATTGACG TATTTACGTA TACTAGGAGA ATAAATCACT
    ACAGCAGGCT AGATAACTGC ATAAATGCAT ATGATCCTCT TATTTAGTGA
                                       MIG1
151 GATAGCTCAT CATTCTATGC AATCATTCCC CAGATTTTGC TCAAATGAAC
    CTATCGAGTA GTAAGATACG TTAGTAAGGG GTCTAAAACG AGTTTACTTG
201 CGATCAAATT AACGTTTAAC AATTTACGGT TTTTCTGGTG GTATTAGCAA
    GCTAGTTTAA TTGCAAATTG TTAAATGCCA AAAAGACCAC CATAATCGTT
        MIG1
251 AATCTGGGGA ATTAATTGTC ACGAGCAGGA TTTTTTGTCA GGATATTCGT
    TTAGACCCCT TAATTAACAG TGCTCGTCCT AAAAAACAGT CCTATAAGCA
             MIG1
301 TTAGTTAGCC CCTCTACTAT GACATTACTT CTCCTGGGAT GGTGACTACG
    AATCAATCGG GGAGATGATA CTGTAATGAA GAGGACCCTA CCACTGATGC
351 ATCTTGTATA AGTATCAGGG TTGATCCCTC CAAATGATAG CTTTCTTCAA
    TAGAACATAT TCATAGTCCC AACTAGGGAG GTTTACTATC GAAAGAAGTT
401 CATCGACTCT CATAATCGAT ATACTTGAAA ACCCAACACA TCACTCAAA
    GTAGCTGAGA GTATTAGCTA TATGAACTTT TGGGTTGTGT AGTGAGTTT
```

Figure 2E

```
                   GAL4
  1  GACAGCCCTC GGATGACACT CCTCCGAGCG TGAGCCTCAG GTCGAGGCCA
     CTGTCGGGAG CCTACTGTGA GGAGGCTCGC ACTCGGAGTC CAGCTCCGGT
                                                     GAL4
 51  TCGCGATGCA CTTACATCAG GTGCCTCGT GCGTTACTAA TGCGGGCCAC
     AGCGCTACGT GAATGTAGTC CACGGAGCA CGCAATGATT ACGCCCGGTG
100  TGTCGTCCGA TCTATTGACG TATTTACGTA TACTAGGAGA ATAAATCGCT
     ACAGCAGGCT AGATAACTGC ATAAATGCAT ATGATCCTCT TATTTAGCGA
                                                MIG1
150  GATAGCTCAT CATTCTATGC AATCATTCCC CAGATTTTGC TCAAATGAAC
     CTATCGAGTA GTAAGATACG TTAGTAAGGG GTCTAAAACG AGTTTACTTG
200  CGATGAAATT AACGTTTAAC AATTTACGGT TTTTCTGGTG GTATTAGTAA
     GCTACTTTAA TTGCAAATTG TTAAATGCCA AAAGACCAC CATAATCATT
         MIG1                                       MIG1
250  AATCTGGGGA ATTAATTTCT AGGGATATTC GTTTAGTTAG CCCCTCTACT
     TTAGACCCCT TAATTAAAGA TCCCTATAAG CAAATCAATC GGGGAGATGA
300  ATGACATTAC TTCTCCTGGG ATGGTGACTA CGATCTTGTA TAAGTATCAG
     TACTGTAATG AAGAGGACCC TACCACTGAT GCTAGAACAT ATTCATAGTC
350  GGTTGATCCC TCCAAATGAT AGCTTTCTTC AACATCGACT CTCATAATCG
     CCAACTAGGG AGGTTTACTA TCGAAAGAAG TTGTAGCTGA GAGTATTAGC
400  ATATACTTGA AAACCCAACA CATCACTCAA A
     TATATGAACT TTTGGGTTGT GTAGTGAGTT T
```

Figure 2F

SYNTHETIC GENE CONTROL REGION

CROSS-REFERENCE TO RELATED APPLICATIONS

This application is the §371 National Stage application of PCT International Application serial no. PCT/US2006/022489, having an international filing date of Jun. 9, 2006, which claims the benefit of U.S. Provisional Application No. 60/690,321, filed Jun. 14, 2005, herein incorporated by reference, now expired.

BACKGROUND OF THE INVENTION

*Saccharomyces cerevisiae*, or baker's yeast, is widely used as a host for the expression of a variety of heterologous polypeptides. Many different proteins from a variety of species have been expressed in *S. cerevisiae*, some to levels of >10% of total cell protein. Typically, expression has been mediated by a plasmid containing a DNA sequence encoding the heterologous polypeptide and the gene control region that controls gene expressions in *S. cerevisiae* as well as other sequences required for the selection and amplification of the plasmid in both *S. cerevisiae* and in *Escherichia coli*. Alternatively, it is also possible to integrate the coding sequence and the gene control region into a *S. cerevisiae* chromosome and achieve high-level expression.

The gene control regions utilized in the expression of heterologous polypeptides in *S. cerevisiae* are typically those which naturally occur in *S. cerevisiae*, e.g., the gene control region for the expression of the divergent GAL1 and GAL10 genes. In contrast, heterologous gene control regions, when used in *S. cerevisiae* cells, have generally been found to be inactive, or lead to aberrant initiation of transcription. It has been proposed that use of *S. cerevisiae* gene control regions is essential for the efficient expression of heterologous genes in *S. cerevisiae* cells. (Romanos et al., YEAST 8:423-488 (1992)).

The references cited herein are not admitted to be prior art to the claimed invention.

SUMMARY OF THE INVENTION

The present invention relates to a synthetic gene control region, which comprises a gene regulatory sequence comprising a binding site for a gene regulatory protein of a yeast strain, and a promoter from a filamentous fungal strain located downstream of the gene regulatory sequence. The filamentous fungal promoter can be recognized by the general transcription factors and RNA polymerase of the yeast strain. The synthetic gene regulatory sequence is capable of regulating transcription initiated by the filamentous fungal promoter in the yeast strain. The binding site for the gene activator is preferably a synthetic binding site.

According to an embodiment of the present invention, the yeast strain is selected from a group consisting of *Saccharomyces cerevisiae, Pichia pastoris, Hansenula polymorpha*, and *Yarrowia lipolytica*. According to a preferred embodiment of the present invention, the yeast strain is *Saccharomyces cerevisiae*. According to an alternative embodiment of the present invention, the yeast strain is *Pichia pastoris*.

The filamentous fungal strain can be selected from the group consisting of *Ustilago maydis, Aspergillus nidulans*, and *Penicillium purpurogenum*. The filamentous fungal promoter can be selected from the group consisting of the promoters for the DPM1 gene of *Ustilago maydis*, ArgB gene of *Aspergillus nidulans*, and XynA gene of *Penicillium purpurogenum*.

According to an embodiment of the present invention, the binding site is for a gene activator of the yeast strain. According to a preferred embodiment of the present invention, the binding site is a binding site for GAL4 protein of *S. cerevisiae*. According to a further preferred embodiment of the present invention, the binding site comprises a sequence selected from the group consisting of SEQ ID NO: 10, 11, 12, and 15, Synthetic GAL4 binding sites.

The gene regulatory sequence can further comprise a binding site for a gene repressor of the yeast strain. According to an embodiment of the present invention, the binding site for a gene repressor is a binding site for the MIG1 protein of *S. cerevisiae*. According to a preferred embodiment of the present invention, the binding site for MIG1 protein comprises a sequence selected from the group consisting of SEQ ID NO: 18, 19, and 20.

According to a preferred embodiment, the synthetic gene control region can comprise a sequence selected from the group consisting of SEQ ID NO: 21, 22, 23, 24, 25, and 26.

The present invention provides DNA expression vectors that comprise the synthetic gene control region, a coding sequence encoding a protein, a polypeptide, or a peptide under the control of the control region, and a yeast selection marker. The coding sequence can encode a eukaryotic, prokaryotic, or viral amino acid sequence. If the yeast strain is *S. cerevisiae*, the selection marker can be selected from the group consisting of LEU2, TRP1, URA3, and HIS3.

The DNA expression vector can further comprise a polyadenylation signal sequence located downstream of the coding sequence. The DNA expression vector can further comprise a transcription terminator located downstream of the coding sequence. The DNA expression vector can further comprise a yeast origin of replication, such as one based on the *S. cerevisiae* 2 micron DNA sequence. The DNA expression vector can further comprises a bacterial origin of replication.

The present invention further provides a yeast strain containing the DNA expression vector. The yeast strain can be selected from the group consisting of *Saccharomyces cerevisiae, Pichia pastoris, Hansenula polymorpha, Yarrowia lipolytica*.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1. The promoters from filamentous fungi. Potential TATA box, transcriptional start site indicated underlined (wave). Putative MIG1 binding site is underlined (broken).

FIG. 1A: truncated XynA promoter sequence (SEQ ID NO: 1).

FIG. 1B: DPM1 promoter sequence (SEQ ID NO: 2).

FIG. 1C: ArgB promoter sequence (SEQ ID NO: 3).

FIG. 2. Synthetic gene control regions comprising the truncated XynA promoter and a gene regulatory region. Putative GAL4 protein binding sites are underlined. Putative MIG1 protein binding sites are underlined (broken).

FIGS. 2A-2F are the DNA sequences of the synthetic gene regulatory regions.

FIG. 2A: EE2-XynA (SEQ ID NO: 21).
FIG. 2B: EE21-XynA (SEQ ID NO: 22).
FIG. 2C: EE22-XynA (SEQ ID NO: 23).
FIG. 2D: EE24-XynA (SEQ ID NO: 24).
FIG. 2E: EE25-XynA (SEQ ID NO: 25).
FIG. 2F: EE26-XynA (SEQ ID NO: 26).

DETAILED DESCRIPTION OF THE INVENTION

Figure 3:
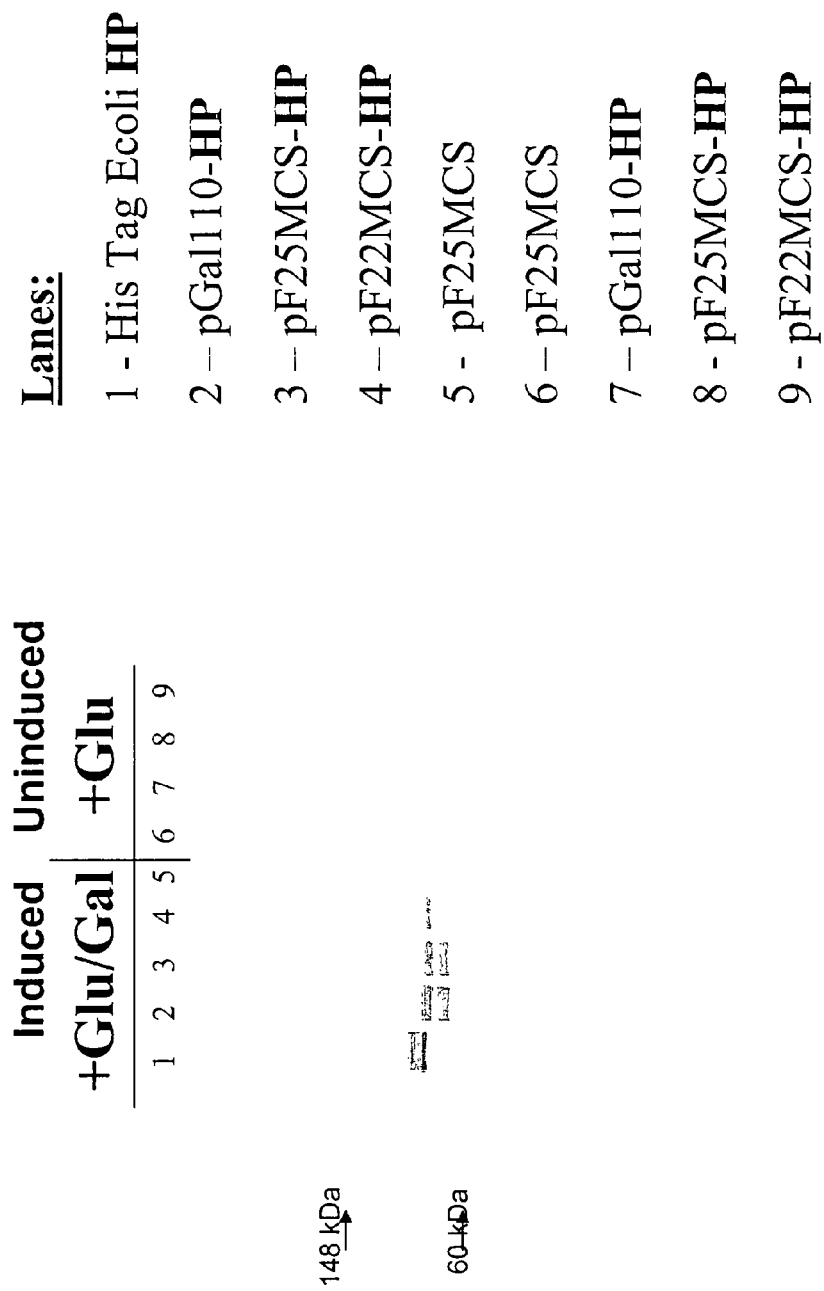
FIG. 3. The expression of a heterologous polypeptide in *S. cerevisiae*, driven by various synthetic gene control regions and the yeast naturally occurring GAL1-GAL10 gene control region, respectively. Lanes 2-5 are samples from yeast cells induced with galactose. Lanes 6-9 are samples from yeast cells grown in the presence of glucose and not induced with galactose.

As discussed above, the gene control regions which are widely used in the expression of heterologous proteins in yeast are typically those which occur naturally in *S. cerevisiae*, (e.g., the gene control region for the expression of the divergent GAL1 and GAL10 genes) and which normally control the expression of the corresponding *S. cerevisiae* genes. In contrast, the present invention provides a synthetic gene control region, which is not known to occur in nature. As used herein, a "gene control region" is the DNA sequence that controls the transcription of a gene, i.e., the rate of transcription initiation. (Alberts, et al., *Molecular Biology of the Cell*, 3$^{rd}$ Edition, Garland Publishing; 1994). The synthetic gene control region of the present invention can be used in the regulation of heterologous gene expression in a yeast strain.

1. The Yeast Strain

As used herein, the term "yeast" refers to any of unicellular eukaryotic organisms that lack chlorophyll and vascular tissue, and reproduce by budding or fission, such as the genus *Saccharomyces*. The genus *Saccharomyces* is composed of a variety of species, including *cerevisiae, carlsbergensis, norbensis, diastaticus, oviformis, uvarum, rouxii, montanus, kluyveri*, and *elongisporus*.

According to a preferred embodiment of the present invention, the yeast strain is *Saccharomyces cerevisiae*. As discussed above, *S. cerevisiae*, is commonly used as a host for the expression of a variety of heterologous polypeptides. The *S. cerevisiae* host cell used for recombinant expression can be selected or engineered to facilitate recombinant gene expression. As the genetic background of a strain can greatly influence the properties of a strain for heterologous protein expression, it was desired to construct yeast strains with differing genetic backgrounds which also contained several desirable genetic markers: mnn9 mutation to prevent hyperglycosylation of secreted proteins, and prb1 and/or pep4 protease mutations to reduce problems with proteolysis (Joyce et al., U.S. Pat. No. 5,820,870). For the synthetic gene control regions containing GAL4 binding sites, over-expression of the GAL4 transcription factor can be achieved in the host *S. cerevisiae* strain, to enhance expression from the control regions (Hopper et al., U.S. Pat. No. 5,068,185).

Moreover, several yeast genera, such as *Hansenula, Candida, Torulopsis*, and *Pichia*, have been shown to contain similar metabolic pathways for the utilization of methanol as a sole carbon source for growth. Moreover, species of other yeast genera can utilize a variety of carbon sources, including galactose, for growth. The yeast strain can be from the families Saccharomycetaceae and Cryptococcaceae, including but not limited to species from the genera *Pichia, Candida, Hansenula, Torulopsis, Kluyveromyces*, and *Saccharomycopsis*.

Specifically, the yeast strain can also be selected from the group consisting of *Pichia pastoris, Hansenula polymorpha, Yarrowia lipolytica, Klyveroinyces lactis, Schizosaccharomyces pombe*, and *Schwanniomyces occidentalis*. These yeast strains were also used as host organism for heterologous gene expression, similar to *Saccharomyces cerevisiae*. (See, e.g., Buckholz and Gleeson, *Bio/Technology* 9:1067-1072 (1991); Gellisen and Hollenberg, *Gene* 190:87-97 (1997); Dominguez, et al., *Int Micobiol.* 1:131-142 (1998)).

According to an embodiment of the present invention, the yeast strain is *Pichia pastoris*. (see, e.g. Werten, et al., *Yeast* 15:1087-1096 (1999); Cregg, et al., *Mol. Biotechnol.* 16, 23-52 (2000))

According to another embodiment of the present invention, the yeast strain is *Hansenula polymorpha*.

According to an embodiment of the present invention, the yeast strain is *Yarrowia lipolytica*. (Muller, et al., *Yeast* 14:1267-1283 (1998); Madzak, et al., *Journal of Biotechnology*, 109:63-81 (2004)).

2. The Synthetic Control Region

The present invention provides a synthetic gene control region that comprises a synthetic gene regulatory sequence comprising a binding site for a gene regulatory protein in a yeast strain, and a promoter from a filamentous fungal strain located downstream of the gene regulatory sequence. The synthetic gene control region is a specific DNA sequence. The sequence of the binding site is preferably not a sequence in the naturally-occurring gene regulatory regions of the yeast strain.

As used herein, the term "filamentous fungus" refers to any of multicellular eukaryotic organisms that lack chlorophyll and vascular tissue, and form a body mass of branched filamentous hyphae that often produce specialized fruiting bodies. Examples of filamentous fungi include *Ustilago maydis, Aspergillus nidulans*, and *Penicillium purpurogenum*.

2.1. The Promoter

Transcription in eukaryotic cells requires that RNA polymerase and general transcription factors assemble at the promoter. As used herein, a "promoter" is the DNA sequence where the RNA polymerase and general transcription factors assemble. A promoter may comprise a TATA box and the start point of transcription. A TATA box is a short sequence of T-A and A-T base pairs that is recognized by TFIID, a general transcription factor. The start point of transcription is typically located 25 base pairs downstream from the TATA box in mammalian cells. ibid. In yeast, the distance from the TATA box to the start of transcription is typically about 100 base pairs.

The promoter of the synthetic gene control region is a promoter from a filamentous fungal strain, which can be recognized by the general transcription factors and RNA polymerase of the yeast strain, such as *S. cerevisiae* (Romanos et al., *YEAST* 8:423-488, (1992)).

Examples of filamentous fungal promoters include those of the XynA gene, DPM1 gene, and the ArgB gene (FIG. 1) (Zimmerman, et al., *Yeast* 12:765-771 (1996), Upshall, et al., *Mol. Gen. Genet.* 204:349-354 (1986), Chavez, et al., *Biol. Res.* 34:217-226 (2001)).

2.2. The Gene Regulatory Sequence

A gene regulatory sequence contains at least one binding site for a gene regulatory protein, whose presence on the DNA affects the rate of transcription initiation. Gene regulatory proteins include gene activators, which stimulate gene expression, and gene repressors, which repress gene expression. The rate of transcription initiation can be increased or decreased by the binding of gene regulatory proteins at the corresponding gene regulatory sequences. As used herein, a "binding site" refers to a DNA sequence in the gene regulatory region to which a gene regulatory protein specifically binds.

The binding sites for a gene regulatory protein were originally identified from naturally-occurring gene regulatory regions. From the identified binding sites for a given gene regulatory protein, a putative consensus binding site sequence can be deduced. According to a preferred embodiment of the present invention, the binding site is a synthetic binding site. As used herein, a "synthetic binding site" refers to the binding site that is not identified from naturally-occurring gene regulatory regions, but rather is constructed taking into account the putative consensus sequence for the gene regulatory protein.

A eukaryotic gene regulatory sequence may be located adjacent to the promoter, far upstream of it, or even downstream of the promoter. (Alberts, et al., *Molecular Biology of the Cell*, 3$^{rd}$ Edition, Garland Publishing; 1994). For example, the gene regulatory sequences of *S. cerevisiae* are usually located a few hundred base pairs upstream of the promoter. The *S. cerevisiae* gene regulatory sequences may stimulate and/or suppress the expression of the gene under its control by binding transcription factors. Examples of gene regulatory sequences include those from GAP (TDH), PGK, TPI, PHO5, ADH2, and CUP1 genes (Romanos et al., *YEAST* 8:423-488, (1992)).

The gene regulatory sequences also determine whether a gene control region is constitutive, i.e., driving the continual expression of the gene, or inducible, i.e., driving gene expression in response to a signal. For example, the gene control regions for GAP (TDH), PGK and TPI genes are constitutive gene control regions. (Romanos et al., *YEAST* 8:423-488 (1992)).

The gene regulatory sequence is preferably an inducible one, which regulates transcription in response to one or more signals. In a variety of recombinant yeast expression systems, such as *S. cerevisiae*, the expression of many different heterologous polypeptides is often shown to be deleterious to the host cell. Consequently, there may be a selective pressure against the expression of such heterologous polypeptides, such that the only cells which accumulate in a scale-up of such a recombinant culture are those which do not express the heterologous polypeptide or express so little of the heterologous polypeptide that the culture becomes an uneconomical source of that polypeptide. An optimal scheme for the scale-up of such a recombinant culture would be to maintain minimal or no expression of the heterologous gene during the expansion of the culture to a large volume and high cell density and then to induce the maximal expression of the heterologous gene only in the final stage of culture growth prior to product isolation. Thus, the synthetic gene control region for recombinant gene expression is preferably an inducible gene control region.

The gene regulatory sequence of GAL1-GAL10 genes of *S. cerevisiae* is an inducible gene regulatory sequence. The GAL1-GAL10 gene regulatory sequence is responsive to both galactose and glucose. It is involved in the regulation of galactose metabolism in *S. cerevisiae*, through controlled expression of the enzymes responsible for the utilization of galactose as a carbon source, e.g., GAL1 (galactokinase) and GAL10 (uridine diphosphogalactose-4-epimerase) (Lohr et al., *FASEB J.* 9:777-787 (1995)). In the absence of galactose, very little expression of these enzymes is detected. If cells initially are grown on medium containing glucose, and galactose is added to the culture, these enzymes are induced coordinately by at least 1000-fold upon depletion of glucose from the media. This induction has been shown to occur at the level of messenger RNA transcription.

Experiments have defined the gene control regions that are necessary and sufficient for galactose induction and are thereby useful for driving the expression of heterologous genes in *Saccharomyces cerevisiae*. GAL1 and GAL10 genes are divergently transcribed. The GAL1-GAL10 gene control region is a sequence of approximately 606 bp located between the two genes, containing the GAL1 and GAL10 promoters and the inducible gene regulatory sequence responsive to galactose and glucose. The 606 bp sequence is used in pGAL110, an approximately 12.0 kbp yeast expression plasmid (Hofmann, et al., *Virology* 209:506-518 (1995)), to drive downstream cloned heterologous gene expression in *S. cerevisiae*.

The GAL1-GAL10 gene regulatory sequence contains the binding sites for GAL4 protein, a yeast gene activator, which is responsive to galactose. Examples of binding sites for GAL 4 protein are presented in table 1.

TABLE 1-1

| SEQ ID NO: | GAL4 binding sites | References |
|---|---|---|
| 4 | CGGATTAGAAGCCGCCG | West, et al., Mol. Cell Biol. 4:2467-2478 (1984) |
| 5 | CGGGTGACAGCCCTCCG | West, et al., Mol. Cell Biol. 4:2467-2478 (1984) |
| 6 | AGGAAGACTCTCCTCCG | West, et al., Mol. Cell Biol. 4:2467-2478 (1984) |
| 7 | CGCGCCGCACTGCTCCG | West, et al., Mol. Cell Biol. 4:2467-2478 (1984) |
| 8 | CGGAGGACTGTCCTCCG | Bram, et al., EMBO J. 5:603-608 (1986) |
| 9 | CGGAGCACTCTCCTCCG | Melcher, et al., Gene 247:53-61 (2000) |

The sequences of SEQ ID NO: 4-9 listed in table 1-2 are GAL4 binding sites identified in the naturally-occurring gene regulatory regions of *S. cerevisiae*.

TABLE 1-2

| SEQ ID NO: | GAL4 binding sites | |
|---|---|---|
| 10 | CGGATGACACTCCTCCG | Putative novel sequence |
| 11 | CGGGCCACTGTCGTCCG | " |
| 12 | GGTCGAGGCCATCCCCG | " |
| 13 | CGGACGACTGTGGTCCG | Bram, et al., EMBO J. 5:603-608 (1986) |
| 14 | CGGGCGACACTCCTCCG | Bram, et al., EMBO J. 5:603-608 (1986) |
| 15 | AGGTCGAGGCCATCCCCG | Bram, et al., EMBO J. 5:603-608 (1986) |

The sequences of SEQ ID NO: 10-12 and SEQ ID NO: 15 listed in table 1-2 are synthetic GAL4 binding sites, which are not identified in the naturally-occurring gene regulatory regions of *S. cerevisiae*. The sequences of SEQ ID NOS: 13 and 14 are GAL4 binding sites identified in the naturally occurring gene regulatory regions of *S. cerevisiae*.

The GAL1-GAL10 gene regulatory sequence also contains the binding sites for MIG1 protein, a yeast gene repressor, which is responsive to glucose. Examples of binding sites for MIG1 protein are presented in table 2.

TABLE 2-1

| SEQ ID NO: | Binding sites for MIG1 | References |
|---|---|---|
| 16 | TATTTCTGGGGTA | Nehlin, et al. EMBO J. 10: 3373-3377 (1991) |
| 17 | GGTTTGTGGGGCC | Nehlin, et al. EMBO J. 10: 3373-3377 (1991) |

The sequences of SEQ ID NO: 16-17 are MIG1 binding sites identified in the naturally-occurring gene regulatory regions of *S. cerevisiae*.

TABLE 2-2

| SEQ ID NO: | Binding sites for MIG1 | |
|---|---|---|
| 18 | GCATACCGGGGCC | Putative novel sequence |
| 19 | ATTATGTGGGGTA | " |
| 20 | AAAATCTGGGGAA | " |

The sequences of SEQ ID NO: 18-20 are synthetic MIG1 binding sites, which are not identified in the naturally-occurring gene regulatory regions of *S. cerevisiae*.

Synthetic gene regulatory regions were constructed to include a filamentous fungal promoter, and binding sites for yeast transcription factors, such as GAL4 and MIG1. According to a preferred embodiment, the synthetic gene regulatory regions are repressed in the presence of glucose, and are activated in the presence of galactose and absence of glucose.

Some examples of synthetic gene regulatory regions are shown in FIG. 2, including EE2-XynA (FIG. 2A, SEQ ID NO: 21), EE21-XynA (FIG. 2B, SEQ ID NO: 22). EE22-XynA (FIG. 2C, SEQ ID NO: 23), EE24-XynA (FIG. 2D, SEQ ID NO: 24), EE25-XynA (FIG. 2E, SEQ ID NO: 25), and EE26-XynA (FIG. 2F, SEQ ID NO: 26).

3. The Expression Vectors

The present invention provides a DNA expression vector, which comprises a synthetic gene control region, a DNA sequence encoding a polypeptide under the control of the control region, and an *S. cerevisiae* selection marker.

3.1 The Components of the Vector

The vector can be an integrating vector, which can be integrated into yeast chromosome, or an episomal vector. In order to be maintained in *S. cerevisiae* cells, an episomal vector needs to contain a replication origin to be replicated. Examples of replication origins include yeast autonomous replication sequences (ARS), and sequences from native 2μ circle of *S. cerevisiae*. The ARS vector can be stabilized by yeast centromeric sequences (CEN). Typically the copy number of a ARS/CEN vector is about 1 or 2 per cell, while the copy number of the 2μ-based vector is about 10 or 40 per cell. (Romanos et al., *YEAST* 8:423-488 (1992))

The expression vector can comprise a yeast selection marker, i.e., a gene encoding a polypeptide for phenotypic selection in yeast. The selection marker can be an auxotrophic selection marker, including LEU2, TRP1, URA3, and HIS3, which are used in corresponding mutant strains that are auxotrophic for leucine, tryptophan, uracil, and histidine, respectively. The selection marker can be a dominant selection marker, such as CUP1, which confers copper-resistance to yeast. Ibid.

The expression vector may need to be replicated in bacterial cells for molecular cloning. Thus, the expression vector can contain a bacterial replication origin. The expression vector can also comprise a bacterial selection marker, i.e., a gene encoding a polypeptide for phenotypic selection in bacteria. The bacterial selection marker can be an antibiotic resistance marker. Examples of bacterial selection marker include genes conferring resistance to ampicillin, kanamycin, tetracycline and chloramphenicol, respectively.

The expression vector can contain a transcriptional terminator located downstream of the heterologous gene for efficient formation of mRNA 3' end. Terminators can be those from TRP1, ADH1, GAP, MFα1, and CYC1. Ibid.

3.2. The Heterologous Coding Sequence Expressed in *S. cerevisiae*

A coding sequence encoding a protein, a polypeptide, or a peptide can be put under the control of the control region in the DNA expression vector. The coding sequence can encode a eukaryotic, prokaryotic, or viral amino acid sequence.

Due to the degeneracy of the genetic code, a large number of different encoding nucleic acid sequences can be used to code for a particular amino acid sequence. The degeneracy of the genetic code arises because almost all amino acids are encoded by different combinations of nucleotide triplets or "codons". Amino acids are encoded by codons as follows:

```
A = Ala = Alanine:          codons GCA, GCC, GCG, GCU

C = Cys = Cysteine:         codons UGC, UGU

D = Asp = Aspartic acid:    codons GAG, GAU

E = Glu = Glutamic acid:    codons GAA, GAG

F = Phe = Phenylalanine:    codons UUC, UUU

G = Gly = Glycine:          codons GGA, GGC, GGG, GGU

H = His = Histidine:        codons CAC, CAU

I = Ile = Isoleucine:       codons AUA, AUC, AUU

K = Lys = Lysine:           codons AAA, AAG

L = Leu = Leucine:          codons UUA, UUG, CUA, CUC, CUG, CUU
```

-continued

```
M = Met = Methionine:    codon AUG

N = Asn = Asparagine:    codons AAC, AAU

P = Pro = Proline:       codons CCA, CCC, CCG, CCU

Q = Gln = Glutamine:     codons CAA, CAG

R = Arg = Arginine:      codons AGA, AGG, CGA, CGC, CGG, CGU

S = Ser = Serine:        codons AGC, AGU, UCA, UCC, UCG, UCU

T = Thr = Threonine:     codons ACA, ACC, ACG, ACU

V = Val = Valine:        codons GUA, GUC, GUG, GUU

W = Trp = Tryptophan:    codon UGG

Y = Tyr = Tyrosine:      codons UAC, UAU
```

If desired, expression of a heterologous polypeptide in a particular host can be enhanced through codon optimization. Codon optimization includes use of more preferred codons. Techniques for codon optimization in different hosts are well known in the art.

Codon optimization for a particular host is performed by replacing codons having a low or moderate usage level with codons having a high usage level. The percentage of optimal codons present in an encoding sequence can vary. In different embodiment the number of optimal codons (including codons initially present and codons introduced) is at least 50%, at least 75%, at least 95%, or 100% of the total number of codons.

Codon optimization can be performed as follows:

1. For a particular codon, compare the wild-type codon frequency to overall codon frequency of use by yeast genes.

2. If the codon is not one of those commonly employed by yeast, replace it with an optimal codon for high expression in yeast cells.

3. Repeat steps (1) and (2) for different codons until achieving the desired level of codon optimization.

4. Inspect the new coding sequence for undesired sequences generated such as unwanted restriction enzyme sites, splice sites, promoters, undesirable palindrome or repeat sequences, transcription terminator sequences, and high frequency of GC bases. Remove undesired sequences using an alternative codon.

Alternative codon usage is defined by Lathe *J. Molec. Biol.*, 183:1-12, 1985. Codon usage in different yeast hosts is well known in the art. For example, Sharp et al., *Yeast* 7:657-678, 1991, describes synonymous codon usage in *Saccharomyces cerevisiae*.

Yeast expression can be achieved using both optimized sequences and sequences not optimized for yeast expression.

Techniques for recombinant gene production, introduction into a cell, and recombinant gene expression are well known in the art. Examples of such techniques are provided in references such as Ausubel, *Current Protocols in Molecular Biology*, John Wiley, 1987-2002, and Sambrook et al., *Molecular Cloning, A Laboratory Manual*, 2$^{nd}$ Edition, Cold Spring Harbor Laboratory Press, 1989.

EXAMPLES

Examples are provided below to further illustrate different features of the present invention. The examples also illustrate useful methodology for practicing the invention. These examples do not limit the claimed invention.

Example 1

Vector Construction

To analyze the ability of synthetic control regions to drive gene expression in *S. cerevisiae*, the GAL1-GAL10 gene control region was removed from pGAL110, through BamHI and XmaI digestion, to form an 11.3 kbp plasmid, pFUNGI. The synthetic gene control regions and a heterologous gene were inserted into pFUNGI. For example, EE22-XynA (FIG. 2C, SEQ ID NO: 25) and EE25-XynA (FIG. 2E, SEQ ID NO: 27) were inserted into pFUNGI with or without an optimized gene encoding a heterologous protein (HP) to form pF22MCS-HP, pF25MCS, and pF25MCS-HP, respectively. The heterologous gene is also inserted into pGAL110 to form pGAL110-HP as a control.

Example 2

*S. cerevisiae* Expression

The vectors were used to transform *S. cerevisiae* strains containing a leu2 mutation to leucine prototrophy (Leu$^+$) by using a spheroplast transformation protocol (Hinnen et al., *Proc. Natl. Acad. Sci. USA*, 75:1929-33, 1978).

Transformants were selected on synthetic agar medium lacking leucine and containing 1.0 M sorbitol. The top and bottom synthetic agar medium lacking leucine and containing 1.0 M sorbitol were obtained from REMEL, Lenexa, Kans. (cat #09459 and 92155, respectively). Clonal Leu$^+$ isolates were obtained by serial growth on SD minus leucine plates (KD MEDICAL, Columbia Md.).

For production in tubes, a 0.3 ml aliquot of the seed culture was transferred to either 5.0 ml of 5× leucine minus medium containing 1.6% glucose, 4% galactose or YEHDG medium for 72 hours at 28-30° C. to a final OD$_{600}$ of 5-16.0/ml. YEHDG medium contains per liter: L-Hy-Soy peptone-Sheffield, 10 g; Yeast extract, 20 g; L-dextrose, 16 g; D (+) galactose, 40 g. For production in flasks, a 1.5-ml aliquot of the seed culture was transferred to 25-ml of medium and grown as described above with shaking at 220 rpm.

After harvesting 10 OD$_{600}$ units of cells per sample, the cell pellets were broken with glass beads in 0.3 ml lysis buffer (0.1 M sodium phosphate buffer, pH 7.2, 0.5 M NaCl, 2 mM PMSF). The lysate was recovered by centrifugation. Protein concentration was determined by Pierce BCA Assay according to the manufacturer's instructions. The cell lysates were analyzed for the expression of the heterologous gene by immunoblot analysis after electrophoresis on Tris-Glycine gels (Invitrogen, Carlsbad, Calif.) in 1× Tris-glycine SDS buffer under reducing and denaturing conditions. The samples contained total cellular protein. The gels were Western transferred onto 0.45 micron nitrocellulose membrane filters (Invitrogen). To estimate protein size, pre-stained standards were run in parallel with the lysates.

Example 3

Heterologous Gene Expression Driven by the Synthetic Gene Control Regions

The heterologous protein was expressed in *E. coli* and *S. cerevisiae* and the expression products were compared.

With the induction by galactose following depletion of glucose, the heterologous protein was expressed in all the transformed *S. cerevisiae* strains tested. The major protein produced by *S. cerevisiae* was detected by Western blot analysis (500 ng protein/lane) with a monoclonal antibody against the heterologous protein (1:5,000), and had a molecular weight of ~105-110-kDa as shown in FIG. 3, (lanes 2, 3 and 4). The ~105-110-kDa protein was slightly smaller than the largest protein band detected in the sample of purified recombinant *E. coli* produced His-tagged heterologous protein (lane 1), as the His-tag added to the molecular weight of the control. No detectable signal was observed with an extract of a control transformant containing the vector pF25MCS alone (lane 5).

The heterologous gene expression level in the strain transformed with pGAL110-HP is comparable to the level of expression obtained from pF25MCS-HP, but greater than that achieved with pF22MCS-HP. Hence, the synthetic gene regulatory region EE25-XynA is as strong as the naturally occurring GAL1-GAL10 gene regulatory region in driving the expression of a heterologous gene in *S. cerevisiae*.

For the cells grown in glucose, no protein bands were observed on Western blots indicating that the heterologous gene was not expressed or expressed at very low levels in transformed *S. cerevisiae* (FIG. 3, lanes 7, 8, and 9). Thus, expression is controlled by the synthetic gene regulatory regions EE22-XynA and EE25-XynA and is repressed in the presence of glucose. This is similar to the repression seen for the GAL1-GAL10 gene naturally occurring regulatory region.

Other embodiments are within the following claims. While several embodiments have been shown and described, various modifications may be made without departing from the spirit and scope of the present invention.

What is claimed is:

1. A synthetic gene control region comprising, a synthetic gene regulatory sequence comprising a binding site for a gene regulatory protein of a yeast strain, and a promoter from a filamentous fungal strain located downstream of the synthetic gene regulatory sequence; wherein the binding site is a binding site for GAL4 protein of *S. cerevisiae*, and the promoter is a promoter for the XynA gene of *Penicillium purpurogenum*, wherein the promoter can be recognized by the general transcription factors and RNA polymerase of the yeast strain; wherein the synthetic gene regulatory sequence is capable of regulating the transcription initiated by a filamentous fungal promoter in the yeast strain.

2. The control region of claim 1 wherein the binding site is not a sequence in the naturally-occurring gene regulatory regions of the yeast strain.

3. The control region of claim 1 wherein the binding site comprises a DNA sequence selected from the group consisting of SEQ ID NO: 8, 9, 10, 11, 12, and 15.

4. The control region of claim 3 wherein the gene regulatory sequence further comprises a binding site for a gene repressor.

5. The control region of claim 4 wherein the binding site for the gene repressor is a binding site for the MIG1 protein of *S. cerevisiae*.

6. The control region of claim 5 wherein the binding site for MIG1 protein comprises a sequence selected from the group consisting of SEQ ID NO: 18, 19, and 20.

7. The control region of claim 1 wherein the synthetic gene control region comprises a sequence selected from the group consisting of SEQ ID NO: 21, 22, 23, 24, 25, and 26.

8. A DNA expression vector comprising, a synthetic gene control region, wherein the synthetic gene control region comprises a sequence selected from the group consisting of SEQ ID NO:21, 22, 23, 24, 25, and 26; a coding sequence encoding a protein, polypeptide, or peptide under the control of the control region, and an yeast selection marker.

9. The DNA expression vector of claim 8 further comprising a polyadenylation signal sequence located downstream of the coding sequence.

10. The DNA expression vector of claim 8 further comprising a transcription terminator located downstream of the coding sequence.

11. The DNA expression vector of claim 8 wherein the yeast selection marker is a *S. cerevisiae* selection marker.

12. The DNA expression vector of claim 11 wherein the *S. cerevisiae* selection marker is selected from the group consisting of LEU2, TRP1, URA3, and HIS3.

13. The DNA expression vector of claim 11 further comprising a *S. cerevisiae* origin of replication.

14. The DNA expression vector of claim 13 wherein the *S. cerevisiae* origin of replication is based on the *S. cerevisiae* 2 micron DNA sequence.

15. The DNA expression vector of claim 8 further comprising a bacterial origin of replication.

16. A yeast strain comprising a DNA expression vector wherein the DNA expression vector comprises, a synthetic gene control region which comprises a sequence selected from the group consisting of SEQ ID NO:21, 22, 23, 24, 25, and 26, a a coding sequence encoding a protein, polypeptide, or peptide under the control of the control region, and an yeast selection marker.

17. A method for producing a recombinant protein, polypeptide, or peptide comprising expressing the coding sequence of the yeast strain of claim 16.

18. The control region of claim 1, wherein the promoter is SEQ ID NO:1.

* * * * *

```
                        SEQUENCE LISTING

<160> NUMBER OF SEQ ID NOS: 26

<210> SEQ ID NO 1
<211> LENGTH: 318
<212> TYPE: DNA
<213> ORGANISM: Penicillium purpurogenum

<400> SEQUENCE: 1
ggatattcgt ttagttagcc cctctactat gacattactt ctcctgggat cctataagca      60
aatcaatcgg ggagatgata ctgtaatgaa gaggaccta ggtgactacg atcttgtata     120
agtatcaggg ttgatccctc caaatgatag ccactgatgc tagaacatat tcatagtccc     180
aactagggag gtttactatc ctttcttcaa catcgactct cataatcgat atacttgaaa     240
acccaacaca gaaagaagtt gtagctgaga gtattagcta tatgaacttt tggggttgtgt    300 tcactcaaaa gtgagttt                                                   318

<210> SEQ ID NO 2
<211> LENGTH: 372
<212> TYPE: DNA
<213> ORGANISM: Ustilago maydis

<400> SEQUENCE: 2
ttgacgacac aaccacggag cgggtgttac ttcttctcac tcacgattct aactgctgtg      60
ttggtgcctc gcccacaatg aagaagagtg agtgctaaga cgattctcga ttcacggttc     120
tcgattctcg ccgtcttggt ctttgggaag gctaagagct aagtgccaag agctaagagc     180
ggcagaacca gaaaccctcc gatcagctgc cgagctggac caccgaccac catcggtctt     240
agctacaaca ctagtcgacg gctcgacctg gtggctggtg gtagccagaa tcgatgttgt     300
accgctccaa atcactcata cacgtctaga atctcatggc gaggtttagt gagtatgtgc     360
agatcttaga gt                                                         372

<210> SEQ ID NO 3
```

<211> LENGTH: 1404
<212> TYPE: DNA
<213> ORGANISM: Aspergillus nidulans

<400> SEQUENCE: 3

```
aagctttatt tcgcggtttt ttggggtagt catctaatga aacagacccg ttcgaaataa      60
agcgccaaaa aacccatca gtagattact ttgtctgggc gacgcagcag aggaagcccc      120
gcgatgactc tataccaccg tacgccgata ctgcgtcgtc tccttcgggg cgctactgag     180
atatggtggc atgcggctat tatcatcatc gcggcgatgg agaagtgggg ttgactccga     240
agacacttca atagtagtag cgccgctacc tcttcacccc aactgaggct tctgtgaagt     300
aaggagcgac gctgttgatt tgtagacgac gcttgatagg gagaagcatt ttcctcgctg     360
cgacaactaa acatctgctg cgaactatcc ctcttcgtaa attgtcgtga tgctcgccca     420
acagaggccg actcgcctca tccgtcataa taacagcact acgagcgggt tgtctccggc     480
tgagcggagt aggcagtatt cgaacgctgt gtaaagcgga gtgggggga aagtgtggat      540
tgtggagagt gcttgcgaca catttcgcct caccccccct ttcacaccta acacctctca     600
atgcgatagt gttgaggctg atcagacggg gaatcgggcc agatatgacc tacgctatca    660
caactccgac tagtctgccg cttagcccgg tctatactgg agtttagagg cctcatttga    720
ctataattta cataaattag ataaatagag tcaaatctcc ggagtaaact gatattaaat    780
gtatttaatc tatttatctc atgaacgcat gcaataattg cagcaaatat tgatgaagcg    840
agaggtagga tacttgcgta cgttattaac gtcgtttata actacttcgc tctccatcct    900
cgatgaagga ctgtgagcag ttcaaggtat cagcagagtc aagggcctga gctacttcct    960
gacactcgtc aagttccata gtcgtctcag ttcccggact tgcaatggcg gtgatccgtg   1020
atcagcgaac ggaaggggcg ctaactctgt acgttaccgc cactaggcac tagtcgcttg   1080
ccttccccgc gattgagaca ttctttacca atgatcggaa gctcctgctg gcggacttat   1140
gagtcattca aagaaatggt tactagcctt cgaggacgac cgcctgaata ctcagtaagt   1200
cgaatcattt ctcagttatt tgtggatgcc ctcgttctgt ccacaatttc gcttagtaaa   1260
gagtcaataa acacctacgg gagcaagaca ggtgttaaag tttccgcccc aagtcttta    1320
agttctttaa catctatatt cttgcacttc aaaggcgggg ttcagaaaat tcaagaaatt   1380
gtagatataa gaacgtgaag cagt                                           1404
```

<210> SEQ ID NO 4
<211> LENGTH: 17
<212> TYPE: DNA
<213> ORGANISM: Saccharomyces cerevisiae

<400> SEQUENCE: 4
cggattagaa gccgccg    17

<210> SEQ ID NO 5
<211> LENGTH: 17
<212> TYPE: DNA
<213> ORGANISM: Saccharomyces cerevisiae

<400> SEQUENCE: 5
cgggtgacag ccctccg    17

<210> SEQ ID NO 6
<211> LENGTH: 17
<212> TYPE: DNA
<213> ORGANISM: Saccharomyces cerevisiae

```
<400> SEQUENCE: 6
aggaagactc tcctccg                                                    17

<210> SEQ ID NO 7
<211> LENGTH: 17
<212> TYPE: DNA
<213> ORGANISM: Saccharomyces cerevisiae

<400> SEQUENCE: 7
cgcgccgcac tgctccg                                                    17

<210> SEQ ID NO 8
<211> LENGTH: 17
<212> TYPE: DNA
<213> ORGANISM: Saccharomyces cerevisiae

<400> SEQUENCE: 8
cggaggactg tcctccg                                                    17

<210> SEQ ID NO 9
<211> LENGTH: 17
<212> TYPE: DNA
<213> ORGANISM: Saccharomyces cerevisiae

<400> SEQUENCE: 9
cggagcactc tcctccg                                                    17

<210> SEQ ID NO 10
<211> LENGTH: 17
<212> TYPE: DNA
<213> ORGANISM: Artificial Sequence
<220> FEATURE:
<223> OTHER INFORMATION: Synthetic GAL4 Binding Site

<400> SEQUENCE: 10
cggatgacac tcctccg                                                    17

<210> SEQ ID NO 11
<211> LENGTH: 17
<212> TYPE: DNA
<213> ORGANISM: Artificial Sequence
<220> FEATURE:
<223> OTHER INFORMATION: Synthetic GAL4 Binding Site

<400> SEQUENCE: 11
cgggccactg tcgtccg                                                    17

<210> SEQ ID NO 12
<211> LENGTH: 17
<212> TYPE: DNA
<213> ORGANISM: Artificial Sequence
<220> FEATURE:
<223> OTHER INFORMATION: Synthetic GAL4 Binding Site

<400> SEQUENCE: 12
ggtcgaggcc atccccg                                                    17

<210> SEQ ID NO 13
<211> LENGTH: 17
<212> TYPE: DNA
<213> ORGANISM: Saccharomyces cerevisiae

<400> SEQUENCE: 13
cggacgactg tggtccg                                                    17
```

```
<210> SEQ ID NO 14
<211> LENGTH: 17
<212> TYPE: DNA
<213> ORGANISM: Saccharomyces cerevisiae

<400> SEQUENCE: 14
cgggcggcac tcctccg                                                    17

<210> SEQ ID NO 15
<211> LENGTH: 17
<212> TYPE: DNA
<213> ORGANISM: Artificial Sequence
<220> FEATURE:
<223> OTHER INFORMATION: Synthetic GAL4 Binding Site

<400> SEQUENCE: 15
aggtcgaggc catcccg                                                    17

<210> SEQ ID NO 16
<211> LENGTH: 13
<212> TYPE: DNA
<213> ORGANISM: Saccharomyces cerevisiae

<400> SEQUENCE: 16
tatttctggg gta                                                        13

<210> SEQ ID NO 17
<211> LENGTH: 13
<212> TYPE: DNA
<213> ORGANISM: Saccharomyces cerevisiae

<400> SEQUENCE: 17
ggtttgtggg gcc                                                        13

<210> SEQ ID NO 18
<211> LENGTH: 13
<212> TYPE: DNA
<213> ORGANISM: Artificial Sequence
<220> FEATURE:
<223> OTHER INFORMATION: Synthetic MIG1 Binding Site

<400> SEQUENCE: 18
gcataccggg gcc                                                        13

<210> SEQ ID NO 19
<211> LENGTH: 13
<212> TYPE: DNA
<213> ORGANISM: Artificial Sequence
<220> FEATURE:
<223> OTHER INFORMATION: Synthetic MIG1 Binding Site

<400> SEQUENCE: 19
attatgtggg gta                                                        13

<210> SEQ ID NO 20
<211> LENGTH: 13
<212> TYPE: DNA
<213> ORGANISM: Artificial Sequence
<220> FEATURE:
<223> OTHER INFORMATION: Synthetic MIG1 Binding Site

<400> SEQUENCE: 20
attatgtggg gta                                                        13

<210> SEQ ID NO 21
```

```
<211> LENGTH: 13
<212> TYPE: DNA
<213> ORGANISM: Artificial Sequence
<220> FEATURE:
<223> OTHER INFORMATION: Synthetic Gene Regulatory Region

<400> SEQUENCE: 21
aaaatctggg gaa                                                            13

<210> SEQ ID NO 22
<211> LENGTH: 872
<212> TYPE: DNA
<213> ORGANISM: Artificial Sequence
<220> FEATURE:
<223> OTHER INFORMATION: Synthetic Gene Regulatory Region

<400> SEQUENCE: 22
gagacagccc tcggagcact ctcctccgag cgtgagcctc aggtcgaggc cactgtcggg          60
agcctcgtga gaggaggctc gcactcgagt tccagctccg gtgatcgcga tgcacttaca         120
tcaggtgcgc tcgtgcgtta ctaatgcgga ggacagcgct acgtgaatgt agtccacgcg         180
agcacgcaat gattacgcct cctgtgtcct ccgatctatt gacgtattta cgtatactag         240
gagaataaat cgctacagga ggctagataa ctgcataaat gcatatgatc tcttatttta         300
gcgamggata gctcgccccg gtatgcaatc attctacata cgttaaaatc gaactactat         360
cgagcggggc catacgttag taagatgtat gcaattttag cttgatcgaa ataggatcg          420 ttttcaatt tacggatatt ctggtggtat tattatgctt atatcctagc aaaaagttaa          480
atgcctataa gaccaccata ataatamgmg tatgtggggt gttaatttct agggatattc         540
gtttagttag cccctctact atacacccca caattaaaga tccctataag caaatcaatc         600
ggggagatga atgacattac ttctcctggg atggtgacta cgatcttgta taagtatcag         660
tactgtaatg aagaggaccc taccactgat gctagaacat attcatagtc ggttgatccc         720
tccaaatgat agctttcttc aacatcgact ctcataatcg ccaactaggg aggtttacta         780
tcgaaagaag ttgtagctga gagtattagc atatcttga aaacccaaca catcactcaa          840
atatatgaac ttttggggttg tgtagtgagt tt                                      872

<210> SEQ ID NO 23
<211> LENGTH: 912
<212> TYPE: DNA
<213> ORGANISM: Artificial Sequence
<220> FEATURE:
<223> OTHER INFORMATION: Synthetic Gene Regulatory Region

<400> SEQUENCE: 23
gagagacagc cctcggagca ctctcctccg tccgtgaccg tcaggtcgag gccactgtcg          60
ggagcctcgt gagaggaggc aggcactggc agtccagctc cggtgatccc gatgcactta        120
catcaggtcc gctcgtgcct actaatccgg aggacaggg ctacgtgaat gtagtccagg         180
cgagcacgga atgattaggc ctcctgtgtc ctccgatcta ttgacgtatt tacgtatact         240
aggagaataa atcgctacag gaggctagat aactgcataa atgcatatga tcctctttatt       300 tagcgamgga tagctcatca ttctatgcaa tcattcccca gattttgcta tcgaactact         360
atcgagtagt aagatacgtt agtaaggggt ctaaaacgat agcttgatcg aatataggat         420
cgtttaacaa tttacggttt ttctggtggt attagcaagc ttatatccta gcaaattgtt         480
aaatgccaaa aagaccacca taatcgttmg aatctgggga attaattgtc cacgagcagg         540 atttttgtc aggatattcg ttagaccct taattaacag gtgctcgtcc taaaaacag            600
```

| | |
|---|---:|
| tcctataagc mgtttagtta gccccctctac tatgacatta cttctcctgg gatggtgact | 660 |
| acaaatcaat cggggagatg atactgtaat gaagaggacc ctaccactga tggatcttgt | 720 |
| ataagtatca gggttgatcc ctccaaatga tagctttctt cactagaaca tattcatagt | 780 |
| cccaactagg gaggtttact atcgaaagaa gtacatcgac tctcataatc gatatacttg | 840 |
| aaaacccaac acatcactca aatgtagctg agagtattag ctatatgaac ttttgggttg | 900 |
| tgtagtgagt tt | 912 |

<210> SEQ ID NO 24
<211> LENGTH: 872
<212> TYPE: DNA
<213> ORGANISM: Artificial Sequence
<220> FEATURE:
<223> OTHER INFORMATION: Synthetic Gene Regulatory Region

<400> SEQUENCE: 24

| | |
|---|---:|
| gagacagccc tcggatgaca ctcctccgag cgtgagcctc aggtagaggc cactgtcggg | 60 |
| agcctactgt gaggaggctc gcactcggag tccatctccg gtgatcgcga tgcacttaca | 120 |
| tcaggtgcgc tcgtgcgtta ctaatgcggg ccacagcgct acgtgaatgt agtccacgcg | 180 |
| agcacgcaat gattacgccc ggtgtgtcgt ccgatctatt gacgtattta cgtatactag | 240 |
| gagaataaat ccgtacagca ggctagataa ctgcataaat gcatatgatc ctcttattta | 300 |
| ggcamggata gctcgccccg gtatgcaatc attctacata cgttaaaatc gaactactat | 360 |
| cgagcggggc catacgttag taagatgtat gcaattttag cttgatcgaa ataggatcg | 420 |
| tttttcaatt tacggatatt ctggtggtat tattatgctt atatcctagc aaaaagttaa | 480 |
| atgcctataa gaccaccata ataatamgmg tatgtggggt gttaatttct agggatattc | 540 |
| gtttagttag cccctctact atacacccca caattaaaga tccctataag caaatcaatc | 600 |
| ggggagatga atgacattac ttctcctggg atggtgacta cgatcttgta taagtatcag | 660 |
| tactgtaatg aagaggaccc taccactgat gctagaacat attcatagtc ggttgatccc | 720 |
| tccaaatgat agctttcttc aacatcgact ctcataatcg ccaactaggg aggtttacta | 780 |
| tcgaaagaag ttgtagctga gagtattagc atatacttga aaacccaaca catcactcaa | 840 |
| atatatgaac ttttgggttg tgtagtgagt tt | 872 |

<210> SEQ ID NO 25
<211> LENGTH: 908
<212> TYPE: DNA
<213> ORGANISM: Artificial Sequence
<220> FEATURE:
<223> OTHER INFORMATION: Synthetic Gene Regulatory Region

<400> SEQUENCE: 25

| | |
|---|---:|
| gagacagccc tcggatgaca ctcctccgag cgtgagcctc aggtcgaggc cactgtcggg | 60 |
| agcctactgt gaggaggctc gcactcggag tccagctccg gtgatcgcga tgcacttaca | 120 |
| tcaggtgcgc tcgtgcgtta ctaatgcggg ccacagcgct acgtgaatgt agtccacgcg | 180 |
| agcacgcaat gattacgccc ggtgtgtcgt ccgatctatt gacgtattta cgtatactag | 240 |
| gagaataaat cactacagca ggctagataa ctgcataaat gcatatgatc ctcttattta | 300 |
| gtgamggata gctcatcatt ctatgcaatc attccccaga ttttgctcaa atgaacctat | 360 |
| cgagtagtaa gatacgttag taaggggtct aaaacgagtt tacttgcgat caaattaacg | 420 |
| tttaacaatt tacggttttt ctggtggtat tagcaagcta gtttaattgc aaattgttaa | 480 |
| atgccaaaaa gaccaccata atcgttmgaa tctggggaat taattgtcac gagcaggatt | 540 |

```
ttttgtcagg atattcgttt agacccctta attaacagtg ctcgtcctaa aaaacagtcc      600
tataagcamg ttagttagcc cctctactat gacattactt ctcctgggat ggtgactacg      660
aatcaatcgg ggagatgata ctgtaatgaa gaggaccta ccactgatgc atcttgtata       720
agtatcaggg ttgatccctc caaatgatag ctttcttcaa tagaacatat tcatagtccc      780
aactagggag gtttactatc gaaagaagtt catcgactct cataatcgat atacttgaaa      840
acccaacaca tcactcaaag tagctgagag tattagctat atgaactttt gggttgtgta      900
gtgagttt                                                               908

<210> SEQ ID NO 26
<211> LENGTH: 870
<212> TYPE: DNA
<213> ORGANISM: Artificial Sequence
<220> FEATURE:
<223> OTHER INFORMATION: Synthetic Gene Regulatory Region

<400> SEQUENCE: 26
gagacagccc tcggatgaca ctcctccgag cgtgagcctc aggtcgaggc cactgtcggg       60
agcctactgt gaggaggctc gcactcggag tccagctccg gtgatcgcga tgcacttaca      120
tcaggtgcct cgtgcgttac taatgcgggc cacagcgcta cgtgaatgta gtccacggag      180
cacgcaatga ttacgccgg tgtgtcgtcc gatctattga cgtatttacg tatactagga      240
gaataaatcg ctacagcagg ctagataact gcataaatgc atatgatcct cttatttagc      300
gamggatagc tcatcattct atgcaatcat tccccagatt ttgctcaaat gaacctatcg      360
agtagtaaga tacgttagta aggggtctaa aacgagttta cttgcgatga aattaacgtt      420
taacaattta cggttttttct ggtggtatta gtaagctact ttaattgcaa attgttaaat      480
gccaaaaaga ccaccataat cattmgmgaa tctggggaat taatttctag ggatattcgt      540
ttagttagcc cctctacttt agacccctta attaaagatc cctataagca aatcaatcgg      600
ggagatgaat gacattactt ctcctgggat ggtgactacg atcttgtata agtatcagta      660
ctgtaatgaa gaggaccta ccactgatgc tagaacatat tcatagtcgg ttgatccctc       720
caaatgatag ctttcttcaa catcgactct cataatcgcc aactagggag gtttactatc      780
gaaagaagtt gtagctgaga gtattagcat atacttgaaa acccaacaca tcactcaaat      840
atatgaactt ttgggttgtg tagtgagttt                                        870
```